United States Patent
Yamamoto

(10) Patent No.: US 11,839,506 B2
(45) Date of Patent: Dec. 12, 2023

(54) X-RAY FLUOROSCOPIC IMAGING APPARATUS AND X-RAY IMAGE PROCESSING METHOD

(71) Applicant: SHIMADZU CORPORATION, Kyoto (JP)

(72) Inventor: Takaya Yamamoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 112 days.

(21) Appl. No.: 17/520,356

(22) Filed: Nov. 5, 2021

(65) Prior Publication Data

US 2022/0183642 A1    Jun. 16, 2022

(30) Foreign Application Priority Data

Dec. 16, 2020  (JP) .................................. 2020-208811

(51) Int. Cl.
*A61B 6/00*  (2006.01)

(52) U.S. Cl.
CPC .............. *A61B 6/487* (2013.01); *A61B 6/461* (2013.01); *A61B 6/481* (2013.01); *A61B 6/504* (2013.01); *A61B 6/5211* (2013.01); *A61B 6/5294* (2013.01)

(58) Field of Classification Search
None
See application file for complete search history.

(56) References Cited

U.S. PATENT DOCUMENTS

| | | | |
|---|---|---|---|
| 2012/0300903 A1* | 11/2012 | Yao ........................ | A61B 6/481 |
| | | | 378/62 |
| 2015/0179148 A1 | 6/2015 | Auvray et al. | |
| 2018/0206809 A1* | 7/2018 | Sato ....................... | A61B 6/503 |
| 2019/0274651 A1* | 9/2019 | Ohashi .................... | A61B 6/486 |
| 2019/0328345 A1* | 10/2019 | Ohashi ................. | A61B 6/5235 |
| 2020/0305828 A1* | 10/2020 | Yoshida ................... | A61B 6/12 |

FOREIGN PATENT DOCUMENTS

| | | |
|---|---|---|
| JP | 2015523183 A | 8/2015 |
| JP | 2019-171105 A | 10/2019 |

OTHER PUBLICATIONS

Notice of Reasons for Refusal with the drafting date of Oct. 12, 2023 and dated Oct. 17, 2023 (together with a machine translation thereof) issued in relation to the corresponding Japanese Patent Application No. 2020-208811.

* cited by examiner

*Primary Examiner* — Hoon K Song
(74) *Attorney, Agent, or Firm* — Muir Patent Law, PLLC

(57) ABSTRACT

This X-ray fluoroscopic imaging apparatus is provided with: an imaging unit; an X-ray image acquisition unit for acquiring an X-ray image; a blood vessel extracted image acquisition unit for acquiring a blood vessel extracted image; a composite image generation unit for generating a second composite image in which the X-ray image and the blood vessel extracted image are composed; and a region of interest setting unit for setting a region of interest in which a device is reflected. The composite image generation unit is configured to generate the second composite image by aligning the positions of the X-ray image and the blood vessel extracted image, based on the device and the blood vessel image reflected in the region of interest.

11 Claims, 12 Drawing Sheets

Second composite image (first frame)

Second composite image (second frame)

Second composite (third frame)

Second composite (fourth frame)

X-RAY FLUOROSCOPIC IMAGING APPARATUS AND X-RAY IMAGE PROCESSING METHOD

CROSS-REFERENCE TO RELATED APPLICATIONS

The priority application number JP2020-208811, entitled "X-ray fluoroscopic imaging apparatus and X-ray image processing method", filed on Dec. 16, 2020, invented by YAMAMOTO Takaya, upon which this patent application is based is hereby incorporated by reference.

BACKGROUND OF THE INVENTION

Field of the Invention

The present invention relates to an X-ray fluoroscopic imaging apparatus and an X-ray image processing method. In particular, the present invention relates to an X-ray fluoroscopic imaging apparatus and an X-ray image processing method for generating a composite image in which a blood vessel extracted image and an X-ray image are aligned in positions.

Description of the Background Art

Conventionally, an X-ray fluoroscopic imaging apparatus for generating a composite image in which a blood vessel extracted image and an X-ray image are aligned in positions has been known as the X-ray fluoroscopic imaging apparatus. Such an X-ray fluoroscopic imaging apparatus is disclosed, for example, in Japanese Unexamined Patent Application Publication No. 2019-171105.

The X-ray fluoroscopic imaging apparatus disclosed in Japanese Unexamined Patent Application Publication No. 2019-171105 is configured to superimpose a blood vessel image captured in advance on a fluoroscopic moving image which is being captured. The X-ray fluoroscopic imaging apparatus disclosed in Japanese Unexamined Patent Application Publication No. 2019-171105 is provided with: a feature point search unit for searching feature points from an image and a moving image; a center of gravity calculation unit for calculating the center of gravity for a plurality of the feature points; a vector group calculation unit for calculating a vector group indicating the relative position of the feature points with reference to the center of gravity; a selection unit for selecting one vector from the vector group; and an image superimposing unit for superimposing the blood vessel image corresponding to the selected vector group on a fluoroscopic moving image. In the X-ray fluoroscopic imaging apparatus disclosed in Japanese Unexamined Patent Application Publication No. 2019-171105, when a device, such as, e.g., a catheter, is introduced into a blood vessel to perform a treatment, an image in which a blood vessel image is superimposed on a fluoroscopic moving image reflecting the device is displayed for an operator.

However, in the configuration disclosed in Japanese Unexamined Patent Application Publication No. 2019-171105, a vector group is calculated based on the feature points reflected in both the blood vessel image and the fluoroscopic moving image, and a superimposed image (composite image) in which a blood vessel image is superimposed on a fluoroscopic moving image is generated. The feature point is reflected in both the blood vessel image and the fluoroscopic moving image, but is not always reflected in the vicinity of the blood vessel into which a device is introduced. Therefore, in a case where there is no feature point in the vicinity of the blood vessel into which a device is introduced, there is a possibility that the error of aligning the positions of the blood vessel image (blood vessel extracted image) and the fluoroscopic moving image (X-ray image) may increase, as the distance between the position of the feature point and the position of the device increases. In other words, in the vicinity of the device in the composite image, there is a possibility that the positional deviation between the blood vessel extracted image and the X-ray image increases.

Note that when an operation for introducing a catheter or another device into a blood vessel is performed, the operator operates the device so as to select the blood vessel into which the device is to be introduced at the blood vessel branch portion while closely observing the vicinity of the device in the blood vessel. Under the circumstance, an X-ray fluoroscopic imaging apparatus capable of generating a composite image in which a positional deviation between an X-ray image and a blood vessel extracted image is suppressed in the vicinity of a device has been desired.

SUMMARY OF THE INVENTION

The present invention has been made to solve the above-described problems. The present invention provides an X-ray fluoroscopic imaging apparatus and an X-ray image processing method capable of suppressing a positional deviation between a blood vessel extracted image and an X-ray image in the vicinity of a device introduced in a blood vessel.

In order to attain the above-described object, an X-ray fluoroscopic imaging apparatus according to a first aspect of the present invention, includes:

an imaging unit including an X-ray source for irradiating an object with X-rays and an X-ray detector for detecting X-rays emitted from the X-ray source;

an X-ray image acquisition unit configured to acquire an X-ray image captured by the imaging unit;

a blood vessel extracted image acquisition unit configured to acquire a blood vessel extracted image in which a blood vessel image of the object is extracted, the blood vessel image having been generated in advance based on a contrast image that is the X-ray image captured with a contrast agent administered to the object;

a composite image generation unit configured to generate a composite image in which the X-ray image captured with no contrast agent administered and the blood vessel extracted image are composed with the X-ray image and the blood vessel extracted image aligned in positions; and a region of interest setting unit configured to set a region of interest, the region of interest being a part of the X-ray image and reflecting a device introduced into a blood vessel of the object, wherein the composite image generation unit is configured to generate the composite image by aligning positions of the X-ray image and the blood vessel extracted image, based on the device reflected in the region of interest set by the region of interest setting unit and the blood vessel image reflected in the blood vessel extracted image.

Further, an X-ray image processing method according to a second aspect of the present invention, includes the steps of:

acquiring an X-ray image;

acquiring a blood vessel extracted image generated in advance based on a contrast image that is the X-ray image captured with a contrast agent administered to an object by a blood vessel extracted image acquisition unit;

generating a composite image in which the X-ray image captured with no contrast agent administered and the blood vessel extracted image are composed with the X-ray image and the blood vessel extracted image aligned in positions by a composite image generation unit;

setting a region of interest by a region of interest setting unit, the region of interest being a part of the X-ray image and reflecting a device introduced into a blood vessel of the subject; and generating the composite image by aligning positions of the X-ray image and the blood vessel extracted image again, based on the device reflected in the region of interest and a blood vessel image reflected in the blood vessel extracted image.

As described above, the X-ray fluoroscopic imaging apparatus according to the first aspect of the present invention is provided with a composite image generation unit configured to generate a composite image by aligning positions of the X-ray image and the blood vessel extracted image based on the device reflected in the region of interest set by the region of interest setting unit and the blood vessel image reflected in the blood vessel extracted image. With this, aligning of the positions of the X-ray image and the blood vessel extracted image is performed based on the device reflected in the region of interest and the blood vessel image reflected in the blood vessel extracted image. Therefore, the aligning of the positions of the X-ray image and the blood vessel extracted image can be performed with high accuracy in the vicinity of the device. As a result, it is possible to generate a composite image in which the positional deviation between the X-ray image and the blood vessel extracted image is suppressed in the vicinity of the device. Note that the vicinity of the device means to include both the position of the device itself and a position around (near) the device.

Further, in the X-ray image processing method according to the second aspect of the present invention, as described above, the method includes a step of generating the composite image by aligning positions of the X-ray image and the blood vessel extracted image again, based on the device reflected in the region of interest and a blood vessel image reflected in the blood vessel extracted image. With this, it is possible to provide an X-ray image processing method capable of generating a composite image in which a positional deviation between the X-ray image and the blood vessel extracted image is suppressed in the vicinity of the device, similarly to the X-ray fluoroscopic imaging apparatus according to the above-described first aspect of the present invention.

DESCRIPTION OF PREFERRED EMBODIMENTS

Configuration of X-Ray Fluoroscopic Imaging Apparatus

Figure 1:
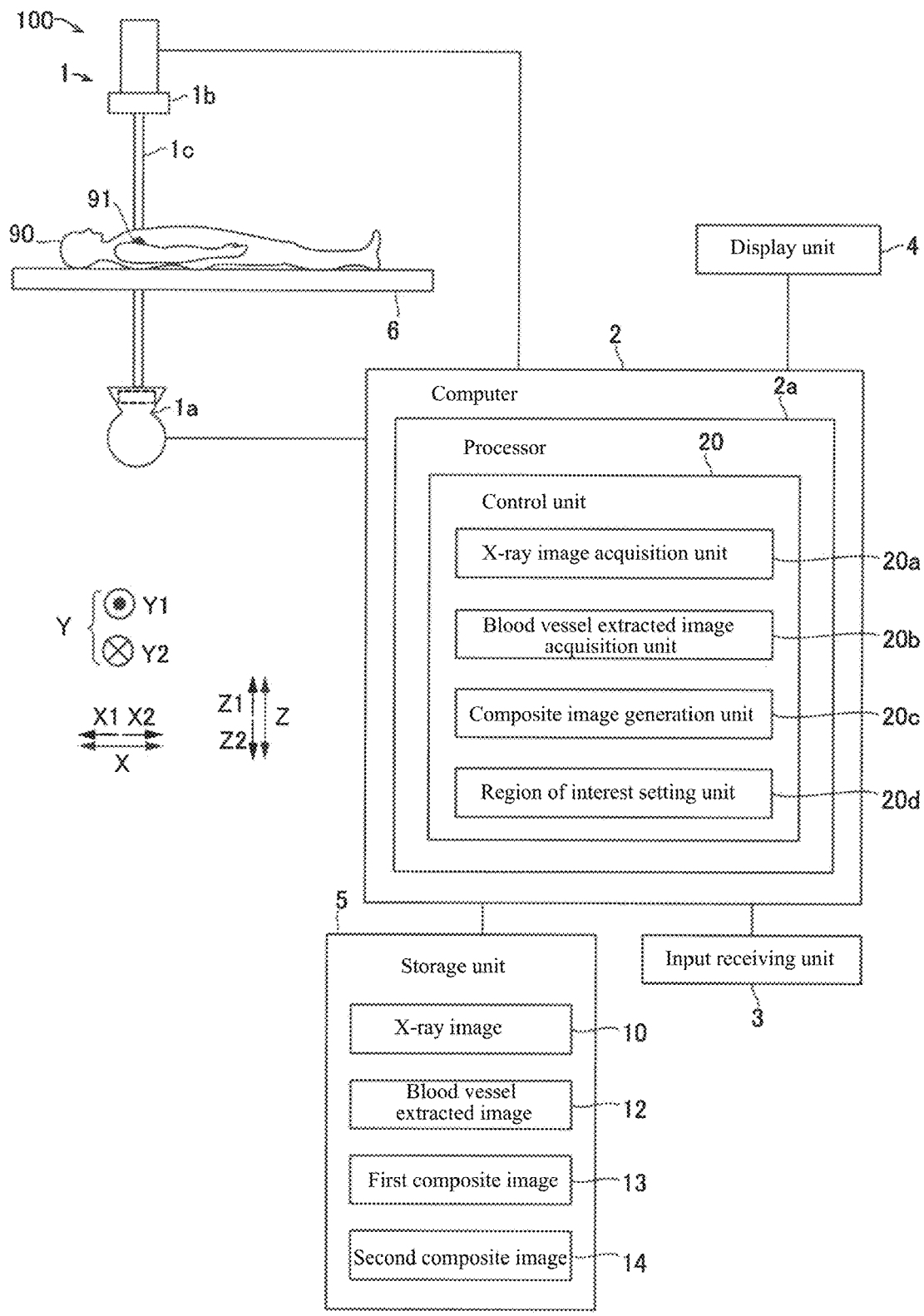
FIG. 1 is a diagram showing an entire configuration of an X-ray fluoroscopic imaging apparatus according to one embodiment.

Referring to FIG. 1, a configuration of an X-ray fluoroscopic imaging apparatus 100 according to one embodiment of the present invention will be described.

As shown in FIG. 1, the X-ray fluoroscopic imaging apparatus 100 according to this embodiment is provided with an imaging unit 1, a computer 2, an input receiving unit 3, a display unit 4, a storage unit 5, and a top board 6. In this embodiment, the X-ray fluoroscopic imaging apparatus 100 images, as an object, the heart 91 of a subject 90. The X-ray fluoroscopic imaging apparatus 100 is used, for example, in a procedure for performing a treatment of, e.g., a stenotic site of a blood vessel 92a of a heart 91, using a device 7.

The imaging unit 1 has an X-ray source 1a, an X-ray detector 1b, and an arm 1c arranged such that the X-ray source 1a and the X-ray detector 1b face to each other.

The X-ray source 1a is configured to irradiate an object with X-rays. Specifically, the X-ray source 1a emits X-rays when a voltage is applied by a drive unit (not shown). The X-ray source 1a has a collimator capable of adjusting the irradiation field, which is the irradiation range of the X-rays. In this embodiment, the X-ray source 1a is attached to the tip end of the arm 1c on one end side.

The X-ray detector 1b is configured to detect the X-rays emitted from the X-ray source 1a. In this embodiment, the X-ray detector 1b is attached to the tip end of the arm 1c on the other end side. That is, the X-ray detector 1b is arranged on the other side of the X-ray source 1a with the top board 6 interposed therebetween. The X-ray detector 1b is configured to be able to detect X-rays. The X-ray detector 1b is, for example, an FPD (Flat Panel Detector). The X-ray detector 1b is configured to detect the X-rays that have passed through an object and outputs a detection signal based on the detected X-rays.

The computer 2 is composed of a processor 2a, such as, e.g., a CPU (Central Processing Unit), a GPU (Graphics Processing Unit), or an FPGA (Field-Programmable Gate Array) configured for image processing, and a ROM (Read Only Memory) and a RAM (Random Access Memory).

As shown in FIG. 1, the processor 2a includes a control unit 20. The control unit 20 is configured to perform the control of the imaging unit 1, etc. The control unit 20 is configured as a software function block to be realized by executing various programs by the processor 2a. The control unit 20 may be configured by hardware by providing a dedicated processor (processing circuit).

As shown in FIG. 1, the control unit 20 is provided with an X-ray image acquisition unit 20a, a blood vessel extracted image acquisition unit 20b, a composite image generation unit 20c, and a region of interest setting unit 20d. The X-ray image acquisition unit 20a, the blood vessel extracted image acquisition unit 20b, the composite image generation unit 20c, and the region of interest setting unit 20d are configured by software functional blocks realized by executing programs for image processing by the control unit 20. The X-ray image acquisition unit 20a, the blood vessel extracted image acquisition unit 20b, the composite image generation unit 20c, and the region of interest setting unit 20d may be individually configured by hardware by providing a dedicated processor (processing circuit).

The X-ray image acquisition unit 20a is configured to acquire an X-ray image 10 captured by the imaging unit 1. Further, the blood vessel extracted image acquisition unit 20b is configured to acquire a blood vessel image 92 (see FIG. 2) of the object previously generated based on the contrast image 11 (see FIG. 3), which is an X-ray image 10 captured in a state in which a contrast agent has been administered to the subject. Further, the composite image generation unit 20c is configured to generate a first composite image 13 and a second composite image 14 in which the X-ray image 10 captured with no contrast agent administered and the blood vessel extracted image 12 are composed with the X-ray image 10 and the blood vessel extracted image 12 aligned in positions. The region of interest setting unit 20d is configured to set a region of interest 30 (see FIG. 5), which is a part of the X-ray image 10 and reflects the device 7 (see FIG. 2) introduced into the blood vessel 92a (see FIG. 2) of the object. The detailed configurations of the X-ray image acquisition unit 20a, the blood vessel extracted image acquisition unit 20b, the composite image generation unit 20c, and the region of interest setting unit 20d will be described later.

The input receiving unit 3 is configured to receive an operation input for setting the region of interest 30 in the X-ray image 10. The input receiving unit 3 includes an input device, such as, e.g., a mouse and a keyboard.

The display unit 4 is configured to display the X-ray image 10 or the second composite image 14. In this embodiment, the display unit 4 displays any one of the X-ray image 10, the first composite image 13, and the second composite image 14. The display unit 4 is a monitor provided on the X-ray fluoroscopic imaging apparatus 100.

The storage unit 5 is configured to store the X-ray image 10 acquired by the X-ray image acquisition unit 20a, the blood vessel extracted image 12 acquired by the blood vessel extracted image acquisition unit 20b, and the first composite image 13 and the second composite image 14 generated by the composite image generation unit 20c. Further, the storage unit 5 is configured to store various programs to be executed by the control unit 20. The storage unit 5 includes a nonvolatile memory, such as, e.g., an HDD (Hard Disk Drive) or an SSD (Solid State Drive).

As shown in FIG. 1, the top board 6 is formed in a rectangular flat plate shape in plan view. The subject 90 is placed on the top board 6 such that the head-foot direction of the subject 90 is along the long side of the rectangle and the left-right direction of the subject 90 is along the short side of the rectangle. Note that in this specification, the head-foot direction of the subject 90 is defined as an X-direction, the left-right direction of the subject 90 is defined as a Y-direction, and the direction perpendicular to the X-direction and the Y-direction is defined as a Z-direction.

A moving mechanism (not shown) is provided to the top board 6. The X-ray fluoroscopic imaging apparatus 100 can image the object while changing the relative position between the top board 6 and the imaging unit 1 by moving the top board 6 in the X-direction by the moving mechanism.

As shown in FIG. 1, an operator (a doctor, a technician, etc.) administers a contrast agent to the subject 90 placed on the top board 6 and captures a plurality of contrast images 11 (see FIG. 3) while changing the relative position between the imaging unit 1 and the top board 6. Prior to the administration of the contrast agent, there is no difference between the attenuation of the X-rays transmitted through the blood vessel 92a (see FIG. 2) and the attenuation of the X-rays transmitted through the surrounding tissue, and therefore an X-ray image 10 in which the blood vessel 92a is clearly reflected cannot be produced. Therefore, a contrast agent for shielding X-rays is administered to the subject 90. As a result, the attenuation amount of the X-rays transmitted through the blood vessel 92a and the attenuation amount of the X-rays transmitted through the surrounding tissue are differentiated from each other, which makes it possible to generate a contrast image 11 in which the blood vessel 92a is clearly reflected.

However, as the dosage of the contrast agent increases, the burden on the subject 90 increases and the visibility of the device 7 in the X-ray image 10 decreases. Thus, when the operator performs the operation using the device 7, the operation is performed without administering the contrast agent to the blood vessel 92a of the subject 90. Therefore, when the operator introduces the device 7 into the blood vessel 92a, in some cases, it may be difficult to visually recognize the blood vessel 92a on the X-ray image 10.

(First Composite Image)

Figure 2:
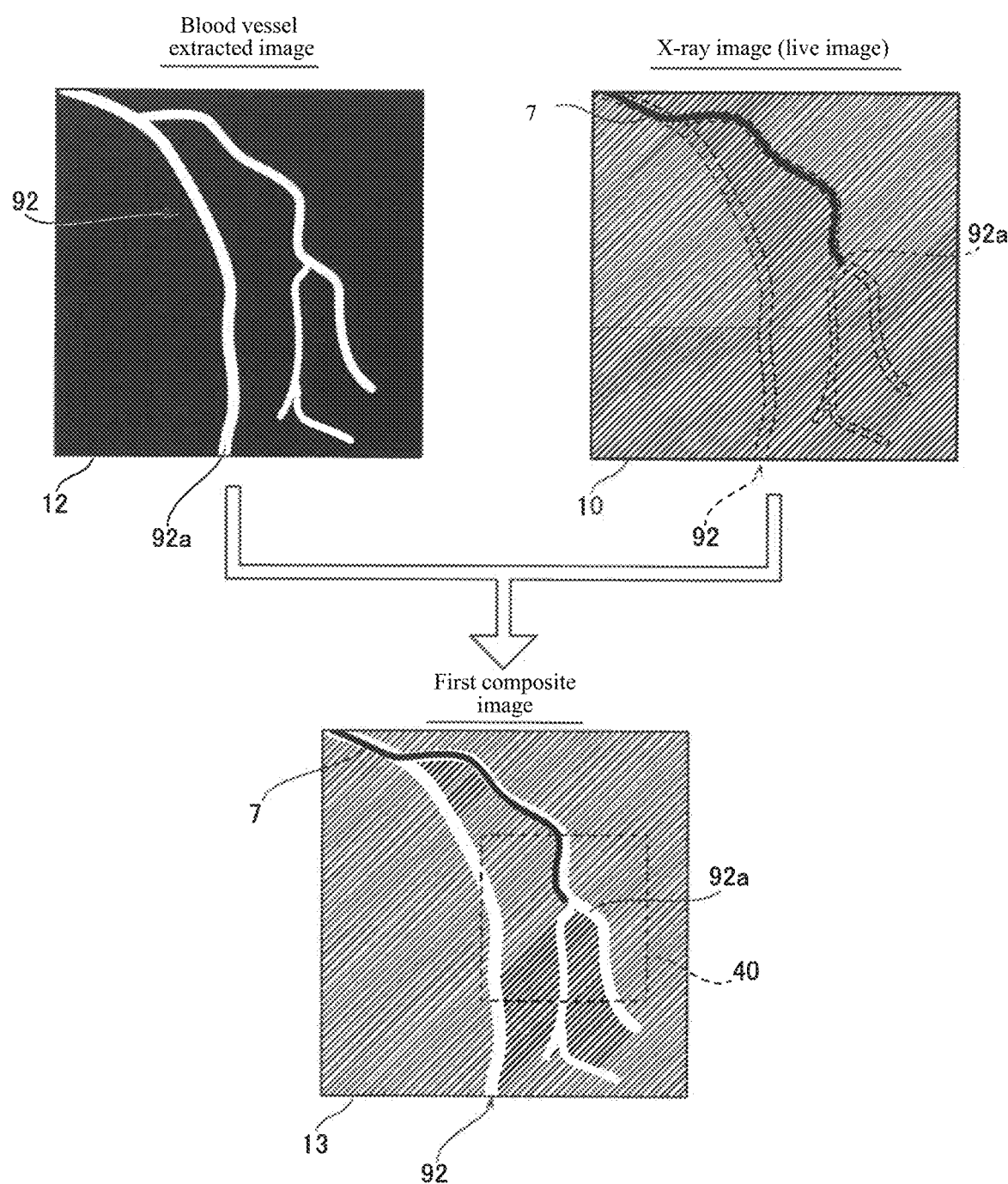
FIG. 2 is a schematic diagram for explaining a configuration in which a composite image generation unit according to one embodiment generates a composite image.

Therefore, in this embodiment, as shown in FIG. 2, the composite image generation unit 20c is configured to generate the first composite image 13 by aligning the positions of the X-ray image 10 and the blood vessel extracted image 12 to each other. Note that in the example shown in FIG. 2, the background of the X-ray image 10 is represented by attaching hatching.

The X-ray image 10 is acquired by the X-ray image acquisition unit 20a. The blood vessel extracted image 12 is acquired by the blood vessel extracted image acquisition unit 20b.

The X-ray image 10 is an image captured with no contrast agent administered to the subject 90 (see FIG. 1). Because it is in a state in which no contrast agent has been administered, in the X-ray image 10, the device 7 is reflected but the blood vessel 92a is not reflected. Note that in the X-ray image 10 shown in FIG. 2, the blood vessel 92a is shown by a broken line for convenience. Further note that the device 7 includes at least one of a catheter, a stent, and a guidewire introduced into the blood vessel 92a. Hereinafter, an example in which a catheter as the device 7 is reflected will be described.

The blood vessel extracted image 12 is an image in which the blood vessel image 92 is reflected. In this embodiment, for convenience, the description will be made by using an image in which only the blood vessel image 92 is reflected as the blood vessel image 92. The blood vessel image 92 is an image of the blood vessel 92a. The details of the blood vessel extracted image 12 will be described later.

The composite image generation unit 20c can generate a first composite image 13 by aligning the positions of the entirety of the X-ray image 10 and the entirety of the blood vessel extracted image 12. Specifically, the composite image generation unit 20c aligns the positions of the X-ray image 10 and the blood vessel extracted image 12 based on the entire shape of the device 7 in the X-ray image 10 and the shape of the blood vessel image 92 of the blood vessel extracted image 12.

(Blood Vessel Extracted Image)

Figure 3:
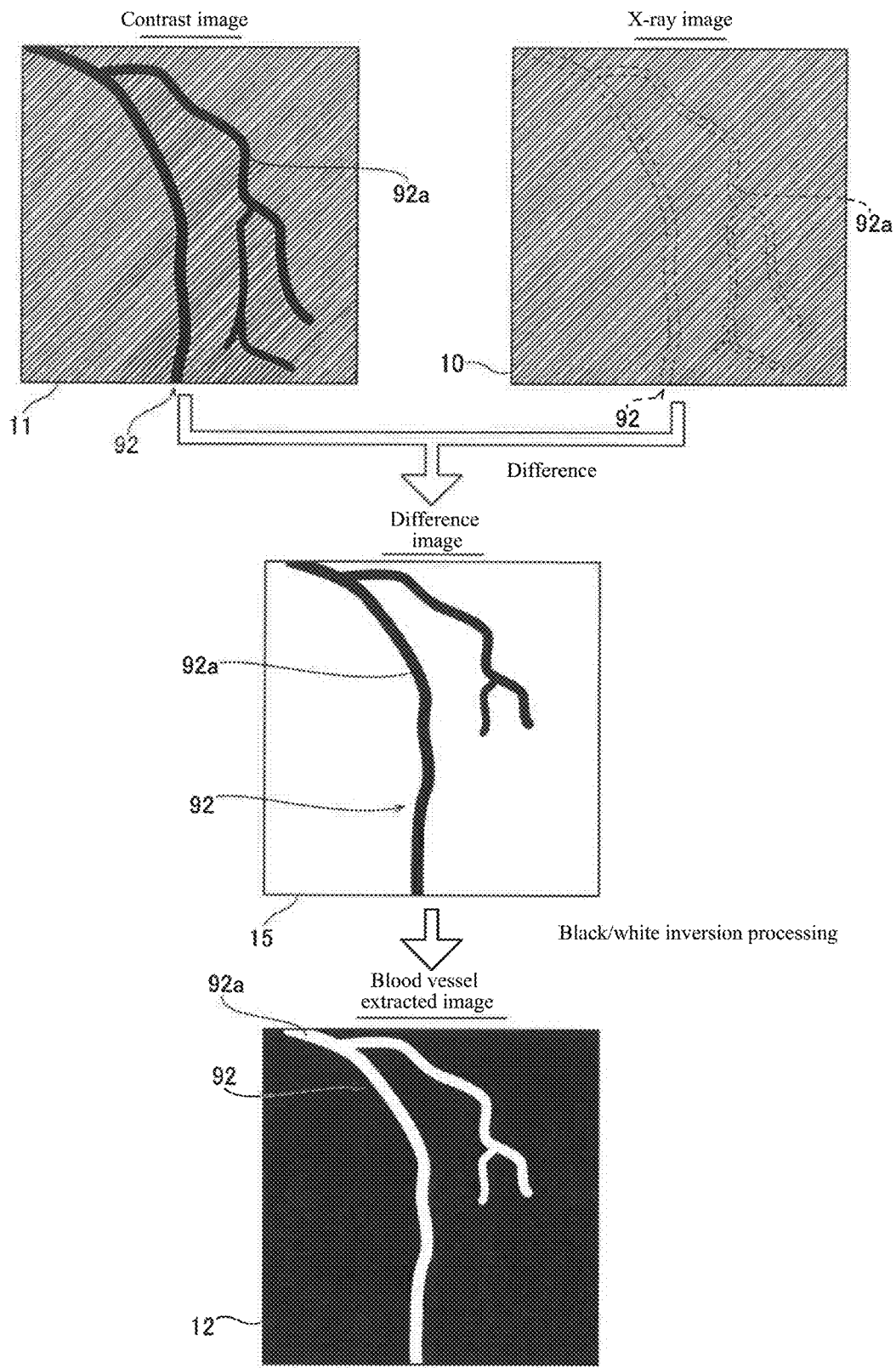
FIG. 3 is a schematic diagram for explaining a blood vessel extracted image acquired by a blood vessel extracted image acquisition unit according to an embodiment.

As shown in FIG. 3, the blood vessel extracted image 12 is generated based on the contrast image 11 captured with a contrast agent administered and the X-ray image 10 captured with no contrast agent administered. Specifically, the blood vessel extracted image 12 is generated by performing black/white inversion processing on a difference image 15 of the contrast image 11 and the X-ray image 10.

The X-ray image 10 is captured with no contrast agent administered, and therefore the blood vessel 92a is not reflected, and only the background portion is reflected. The contrast image 11 is captured with a contrast agent administered, the blood vessel 92a and the background area are reflected. Therefore, only the blood vessel 92a is reflected in the difference image 15 between the contrast image 11 and the X-ray image 10. Note that in the contrast image 11, the background is shown by attaching hatching.

The blood vessel extracted image 12 is generated by performing black/white inversion processing, which is processing for inverting the brightness of the difference image 15. In the blood vessel extracted image 12, the blood vessel image 92, which is the image of the blood vessel 92a, is depicted in white, and the portions other than the blood vessel 92a are depicted in black.

(Positional Deviation in Composite Image)

Figure 4:
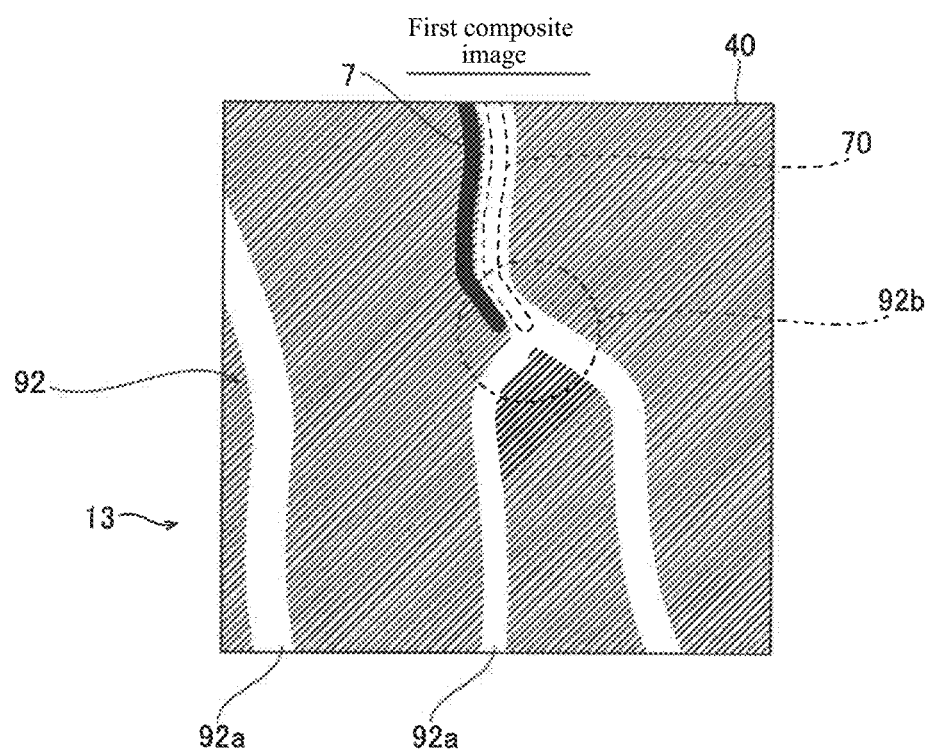
FIG. 4 is a schematic diagram for explaining the positional deviation between the X-ray image and the blood vessel extracted image.

In the configuration shown in FIG. 2, the composite image generation unit 20c aligns the positions of the entirety of the X-ray image 10 and the entirety of the blood vessel extracted image 12. The X-ray image 10 and the blood vessel extracted image 12 are images captured at different times (timings) and may not completely coincide with each other. Therefore, when aligning the positions of the entirety of the X-ray image 10 and the entirety of the blood vessel extracted image 12 to each other, if it is attempted to minimize the entire error, a positional deviation exists locally. That is, as in the first composite image 13 shown in FIG. 4, in the first composite image 13, a positional deviation may occur between the device 7 and the blood vessel image 92. Note that FIG. 4 is an enlarged schematic diagram of the region 40 surrounded by a broken line in FIG. 2. In the example shown in FIG. 4, a virtual device 70 is illustrated by a broken line at a position of the device 7 in the case where no positional deviation has occurred.

Further, for example, it may be conceivable that a gold marker or the like which will be reflected in both the X-ray image 10 and the blood vessel extracted image 12 is introduced into the subject 90, and both the images are aligned in positions based on the gold marker reflected in both the X-ray image 10 and the blood vessel extracted image 12. However, even in a case where both the images are aligned in positions based on the gold marker, both the images coincide accurately around the position of the gold marker, but an error increases as the distance from the gold marker increases.

As shown in FIG. 4, in a case where the positions of the device 7 and the blood vessel image 92 deviate, it becomes difficult for an operator to correctly move the device 7 at the branch portion 92b or the like of the blood vessel 92a.

(Second Composite Image)

Figure 5:
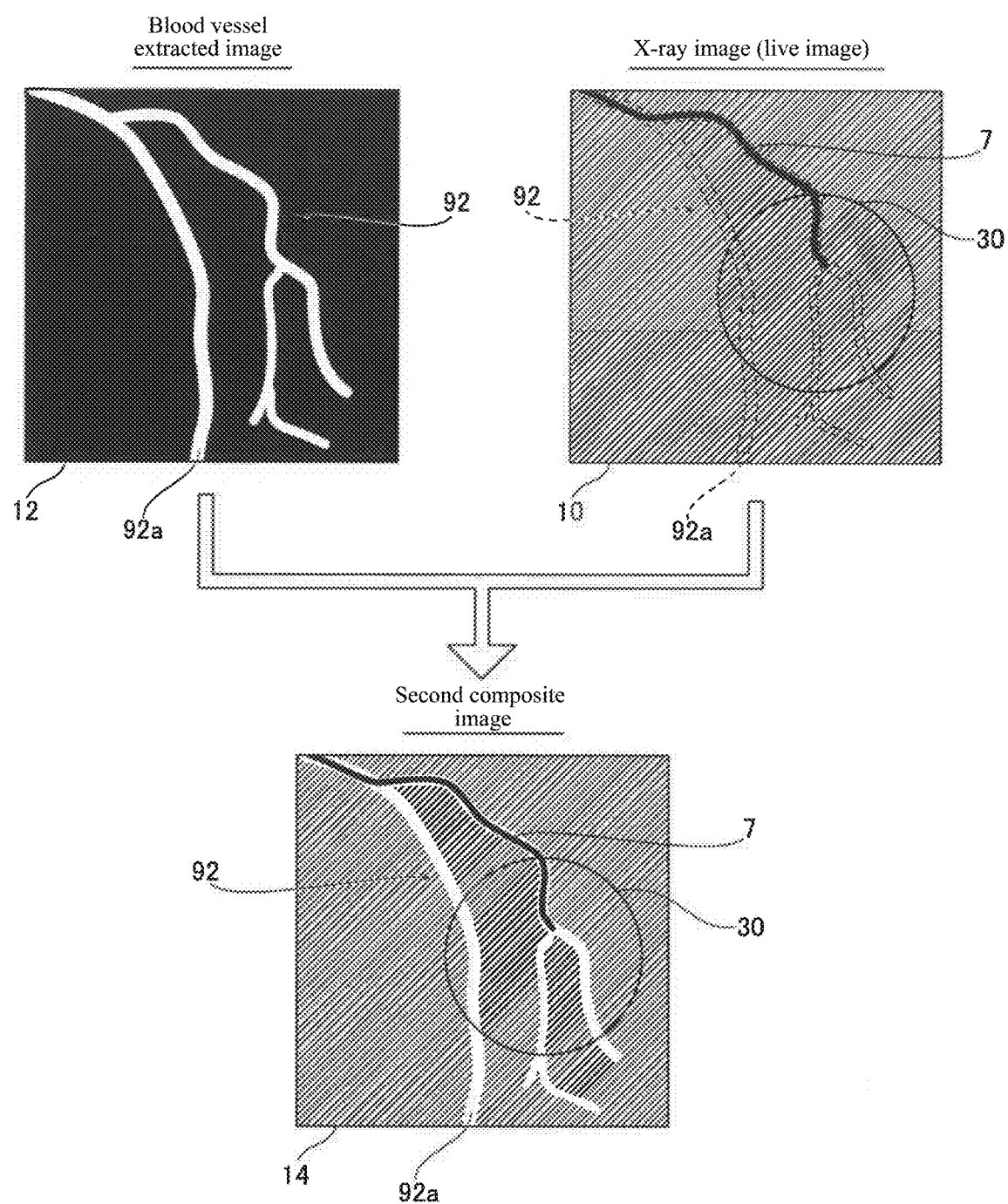
FIG. 5 is a schematic diagram for explaining a configuration of generating a composite image by a composite image generation unit according to one embodiment in a case where a region of interest is set.

Therefore, in this embodiment, as shown in FIG. 5, the composite image generation unit 20c (see FIG. 1) is configured to generate a second composite image 14 by aligning the positions of the X-ray image 10 and the blood vessel extracted image 12 to each other based on the device 7 reflected in the region of interest 30 set by the region of interest setting unit 20d (see FIG. 1) and the blood vessel image 92 reflected in the blood vessel extracted image 12.

As shown in FIG. 5, the region of interest setting unit 20d is configured to set the region of interest 30 in the X-ray image 10, based on an operation input received by the input receiving unit 3. Specifically, the region of interest setting unit 20d sets, in the X-ray image 10, a region of interest 30 of a predetermined shape and a predetermined size at a position based on an operation input received by the input receiving unit 3. In the example shown in FIG. 5, the region of interest setting unit 20d sets the region of interest 30 of a circular shape in the X-ray image 10. The size of the region of interest 30 will be described later.

In this embodiment, the composite image generation unit 20c is configured to generate a second composite image 14 by aligning the positions of the X-ray image 10 and the blood vessel extracted image 12 to each other based the device 7 reflected in the region of interest 30 when the region of interest 30 is set by the region of interest setting unit 20d that has received an operation input in a state in which the X-ray image 10 or the first composite image 13 is being displayed on the display unit 4. That is, in a case where a certain positional deviation is allowed, such as when introducing the device 7 into a thick blood vessel 92a or the like, the first composite image 13 in which the entire X-ray image 10 and the entire blood vessel extracted image 12 have been aligned in the positions is displayed on the display unit 4. Further, in a case where the device 7 reaches a position where no positional deviation is allowed, such as the branch portion 92b of the blood vessel 92a, the second composite image 14 generated by aligning the positions of the X-ray image 10 and the blood vessel extracted image 12 to each other based on the device 7 reflected in the region of interest 30 set based on an operation input of an operator may be displayed on the display unit 4.

(Composite Image as Moving Image)

Figure 6:
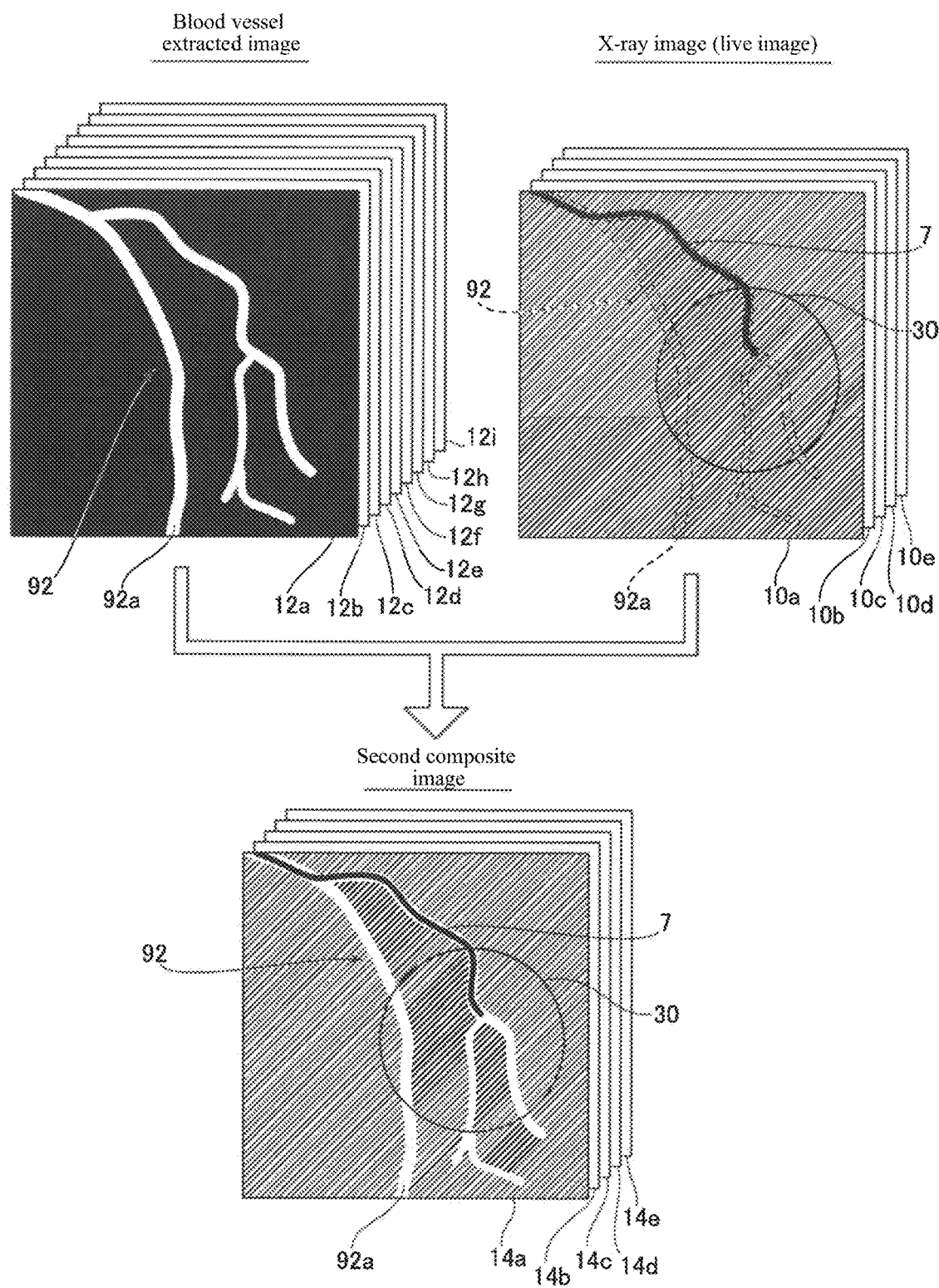
FIG. 6 is a schematic diagram for explaining a composite image as a moving image generated by a composite image generation unit according to one embodiment.

As shown in FIG. 6, in this embodiment, the X-ray image acquisition unit 20a is configured to acquire the X-ray image 10 to be sequentially generated as a live image. Further, the composite image generation unit 20c is configured to generate a second composite image 14 by acquiring a region 31 (see FIG. 7) corresponding to the region of interest 30 in the blood vessel extracted image 12 based on the device 7 reflected in the region of interest 30 of each frame of the live image and aligning the positions of the region 31 corresponding to the region of interest 30 in the acquired blood vessel extracted image 12 and the region of interest 30 of each frame of the live image. Note that acquiring the region 31 corresponding to the region of interest 30 means acquiring the position (position coordinate) of the region 31 corresponding to the region of interest 30 in the blood vessel extracted image 12.

The X-ray image acquisition unit 20a is configured to acquire, as live images, a plurality of X-ray images 10 for at least one period of the heartbeat of the heart 91. The X-ray image 10 is a live image captured at a given frame rate. The predetermined frame rate is, for example, 15 fps (frames per second) or 7.5 fps. Note that in FIG. 6, for convenience, an example is shown in which the X-ray image acquisition unit 20a acquires, as live images, five frames of X-ray images, i.e., the X-ray image 10a, the X-ray image 10b, the X-ray image 10c, the X-ray image 10d, and, the X-ray image 10e.

Further, the blood vessel extracted image acquisition unit 20b is configured to acquire, as blood vessel extracted images 12, at least a plurality of blood vessel extracted images 12 for one period of the heartbeat of the heart 91. Note that the blood vessel extracted image 12 is an image showing the position of the blood vessel 92a in the X-ray image 10. Therefore, the blood vessel extracted image 12 is preferably captured at a frame rate higher than that of the X-ray image 10 in order to acquire a frame corresponding to the blood vessel 92a in the X-ray image 10. For example, the blood vessel extracted image 12 is preferably captured at 30 fps. In FIG. 6, for convenience, an example is shown in which the blood vessel extracted image acquisition unit 20b acquires, as blood vessel extracted images 12, blood vessel extracted images of nine frames, i.e., the blood vessel extracted image 12a, the blood vessel extracted image 12b, the blood vessel extracted image 12c, the blood vessel extracted image 12d, the blood vessel extracted image 12e, the blood vessel extracted image 12f, the blood vessel extracted image 12g, the blood vessel extracted image 12h, and the blood vessel extracted image 12i.

The composite image generation unit 20c generates a second composite image 14 as a moving image by aligning the positions of the blood vessel extracted image 12 for each frame of the live image (X-ray image 10). Specifically, the composite image generation unit 20c generates a second composite image 14 on a frame-by-frame base by performing the alignment of the position of the blood vessel extracted image 12 out of a plurality of blood vessel extracted images 12, for each frame of the X-ray image 10. In FIG. 6, for convenience, an example is shown in which the composite image generation unit 20c generates second composite images 14 of five frames, i.e., the second composite image 14a, the second composite image 14b, the second composite image 14c, the second composite image 14d, and the second composite image 14e.

(Acquisition of Region Corresponding to Region of Interest)

Here, the composite image generation unit 20c selects an image out of the plurality of blood vessel extracted images 12 to be aligned in the position with the X-ray image 10. Specifically, the composite image generation unit 20c selects a blood vessel extracted image 12 to be aligned in the position based on the shape of the device 7 in the X-ray image 10 and the shape of the blood vessel image 92 in the blood vessel extracted image 12. More specifically, in order to align the positions of the X-ray image 10 and the blood vessel extracted image 12 based on the region of interest 30, the composite image generation unit 20c selects a blood vessel extracted image 12 to be aligned in the position by acquiring a portion corresponding to the region of interest 30 in the blood vessel extracted image 12.

However, as shown in FIG. 6, the device 7 is reflected in the X-ray image 10, but the device 7 is not reflected in the blood vessel extracted image 12. Therefore, in this embodiment, the composite image generation unit 20c is configured to acquire a region 31 (see FIG. 7) corresponding to the region of interest 30 from the blood vessel extracted image 12 having a phase closest to the phase of each frame of the live image in the region of interest 30 among the plurality of blood vessel extracted images 12, based on the shape of the device 7 in the region of interest 30 in the blood vessel extracted image of each frame of the live image and the shape of the blood vessel image 92 reflected in the blood vessel extracted image 12.

Figure 7:
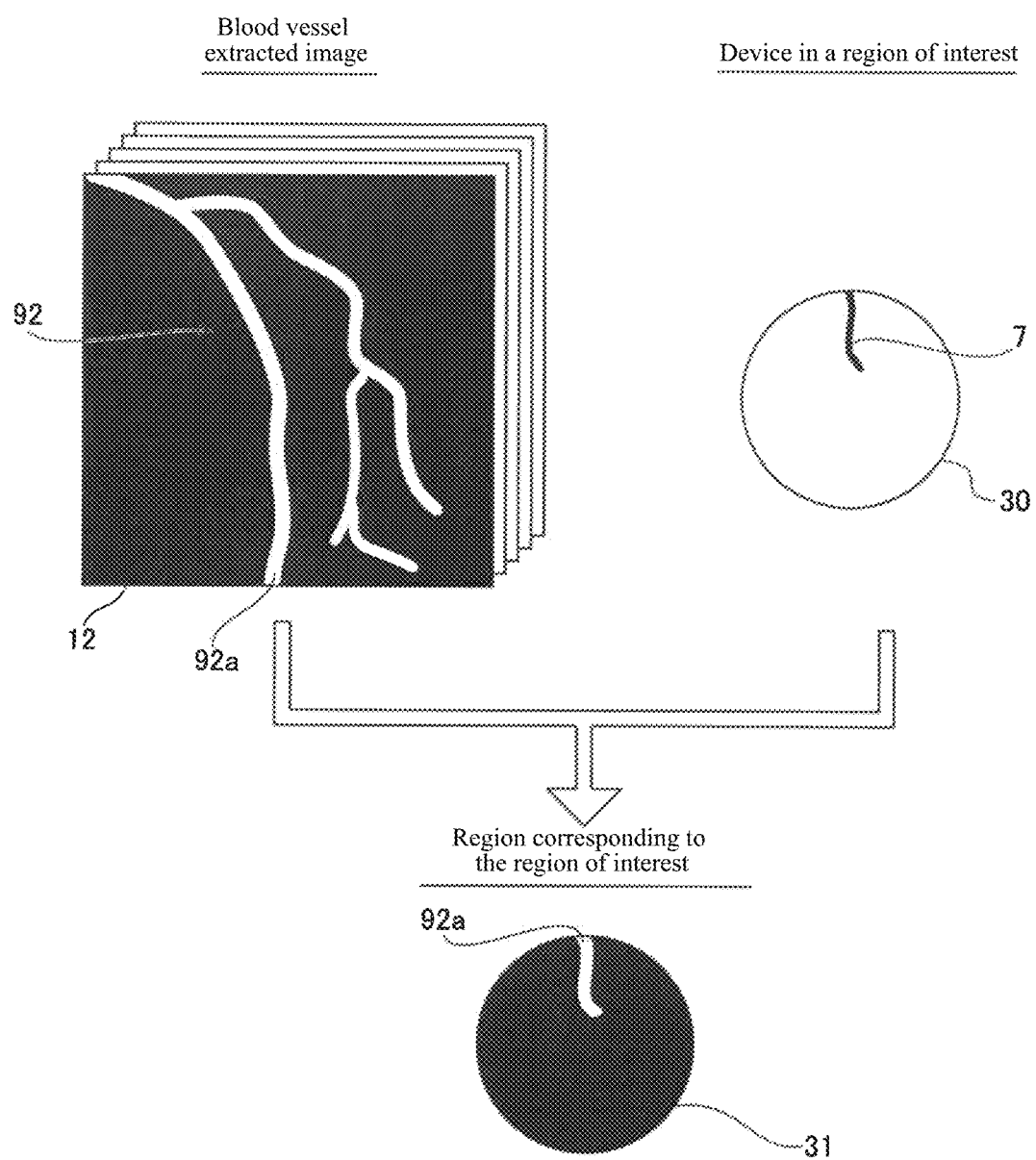
FIG. 7 is a schematic diagram for explaining a configuration in which a composite image generation unit acquires a region corresponding to a region of interest according to one embodiment.

In this embodiment, as shown in FIG. 7, the composite image generation unit 20c is configured to acquire the region 31 corresponding to the region of interest 30 in the blood vessel extracted image 12, based on the shape of the device 7 reflected in the region of interest 30 and the shape of the blood vessel image 92 reflected in the blood vessel extracted image 12.

The device 7 advances through the blood vessel 92a, and therefore the device 7 is reflected in the X-ray image 10 in a shape along the blood vessel 92a. As a result, the shape of the device 7 in the X-ray image 10 and the contour of the blood vessel image 92 in the blood vessel extracted image 12 or the curve passing through the center of the blood vessel image 92 coincide with each other with high accuracy. Therefore, in this embodiment, for example, the composite image generation unit 20c acquires, as the region 31 corresponding to the region of interest 30, a region of the blood vessel extracted image 12 highly correlated with the shape of the device 7 reflected in the region of interest 30 by shape-fitting the shape of the device 7 reflected in the region of interest 30 and the shape of the blood vessel image 92 reflected in the blood vessel extracted image 12. Note that other known techniques may be used for acquiring the region 31 corresponding to the region of interest 30.

(Position Aligning by Region of Interest and Region Corresponding to Region of Interest)

Figure 8:
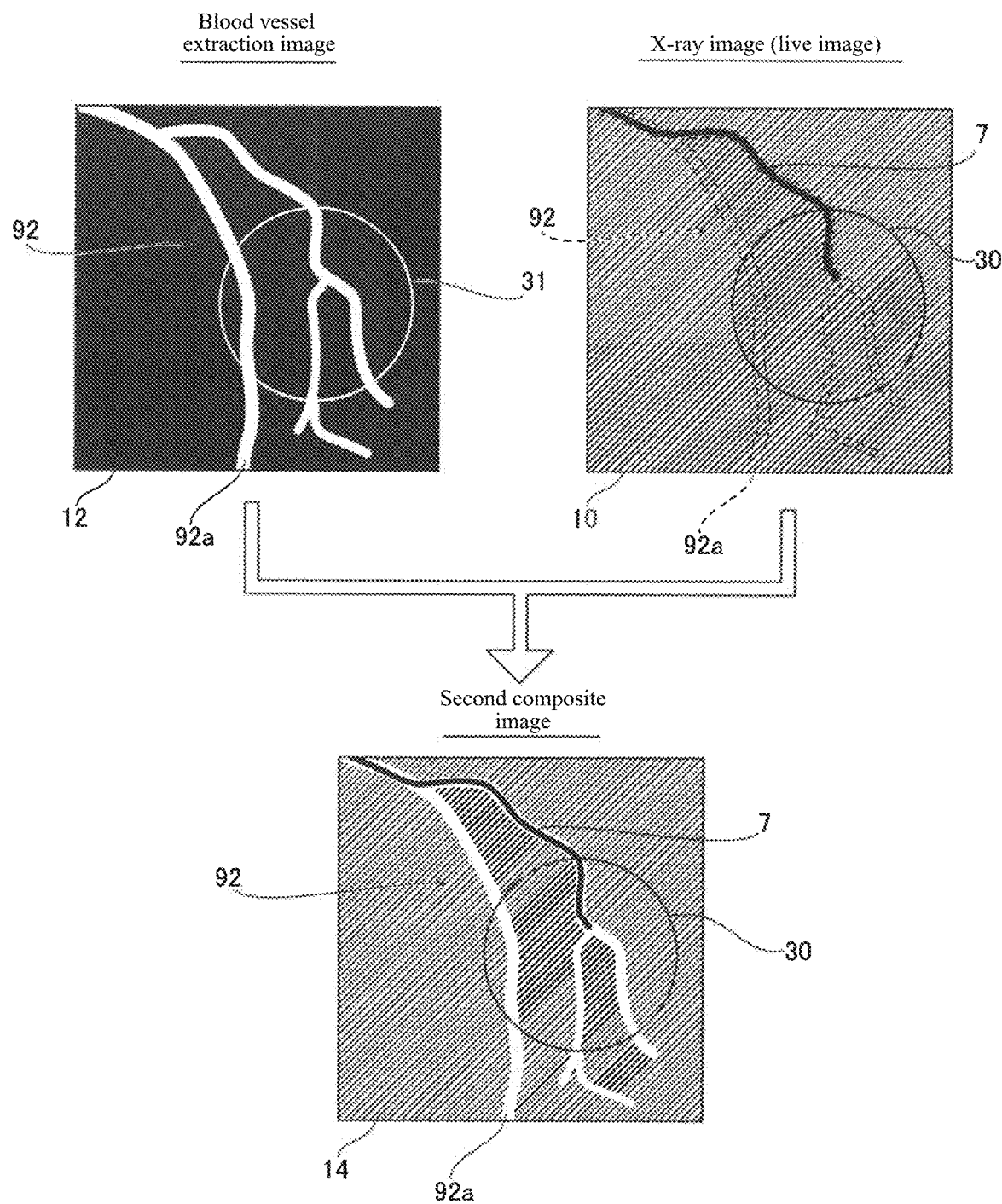
FIG. 8 is a schematic diagram for explaining a configuration for aligning positions of the X-ray image and the blood vessel extracted image based on a region of interest and a region corresponding to the region of interest by a composite image generation unit according to one embodiment.

As shown in FIG. 8, the composite image generation unit 20c aligns the positions of the X-ray image 10 and the blood vessel extracted image 12, based on the region of interest 30 in the X-ray image 10 and the region 31 corresponding to the region of interest 30 in the blood vessel extracted image 12. Specifically, the composite image generation unit 20c aligns the positions of the X-ray image 10 and the blood vessel extracted image 12, based on the shape of the device 7 reflected in the region of interest 30 and the shape of the blood vessel image 92 reflected in the blood vessel extracted image 12.

(Size of Region of Interest)

Figure 9A:
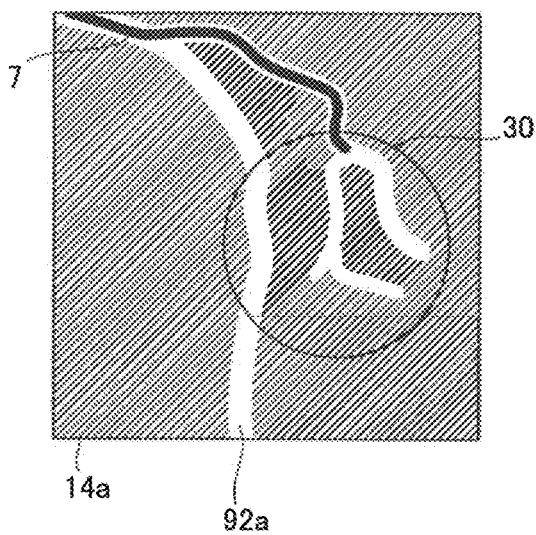
FIG. 9A is a schematic diagram of a first frame of a second composite image for explaining a size of a region of interest set by a region of interest setting unit according to one embodiment.
Figure 9B:
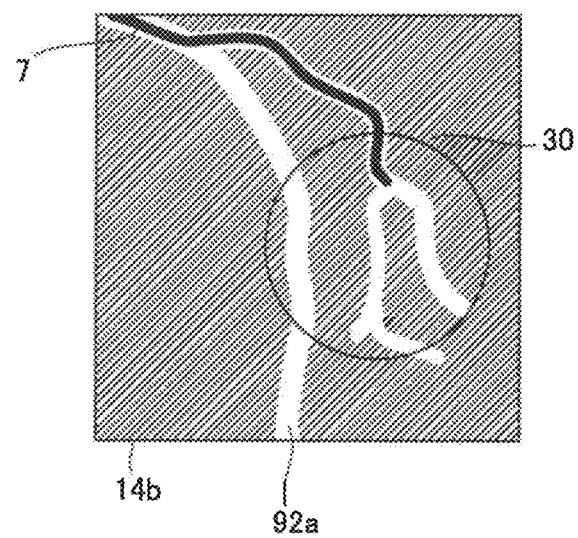
FIG. 9B is a schematic diagram of a second frame of a second composite image for explaining a size of a region of interest set by a region of interest setting unit according to one embodiment.
Figure 9C:
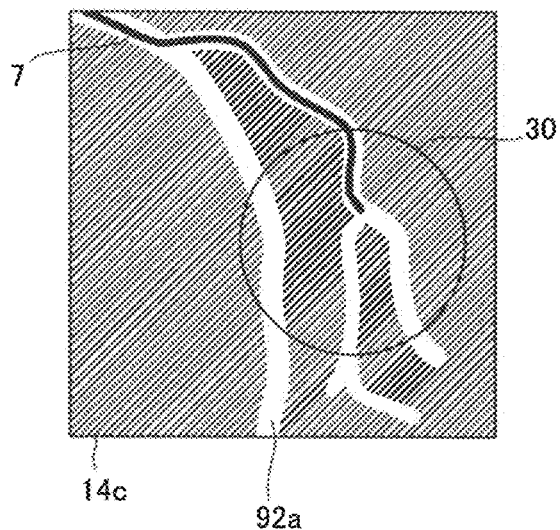
FIG. 9C is a schematic diagram of a third frame of a second composite image for explaining a size of a region of interest set by a region of interest setting unit according to one embodiment.
Figure 9D:
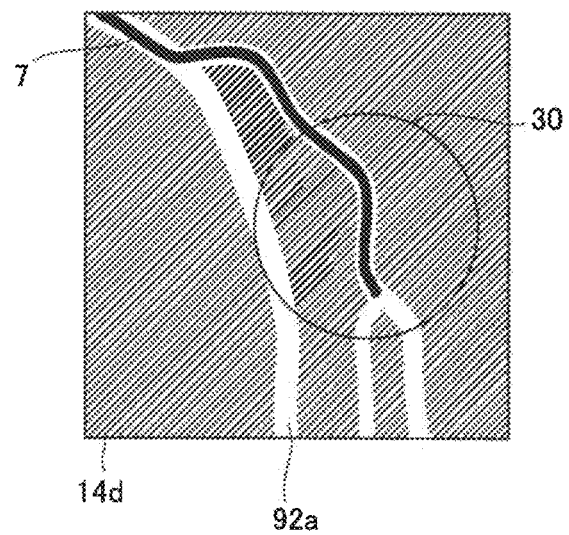
FIG. 9D is a schematic diagram of a fourth frame of a second composite image for explaining a size of a region of interest set by a region of interest setting unit according to one embodiment.

FIGS. 9A to 9D show a second composite image 14a to a second composite image 14d, i.e., the first frame to the fourth frame of the second composite image 14 as moving images. In this embodiment, since the object is the heart 91 (see FIG. 1) of the subject 90 (see FIG. 1), the device 7 and the blood vessel 92*a* displayed on the second composite image 14 are moved in accordance with the heartbeat of the heart 91. In this embodiment, the region of interest setting unit 20*d* is configured to set the region of interest 30 of a size corresponding to the moving range of the device 7 when the device 7 moves in accordance with the heartbeat of the heart 91 to the live image (X-ray image 10). That is, the size of the region of interest 30 is set such that the device 7 is reflected in the region of interest 30 in either the case where the device 7 is moved to the uppermost side in the second composite image 14 as shown in FIG. 9A or the case where the device 7 is moved to the lowermost side in the second composite image 14 as shown in FIG. 9D.

(Region of Interest Reset)

Figure 10:
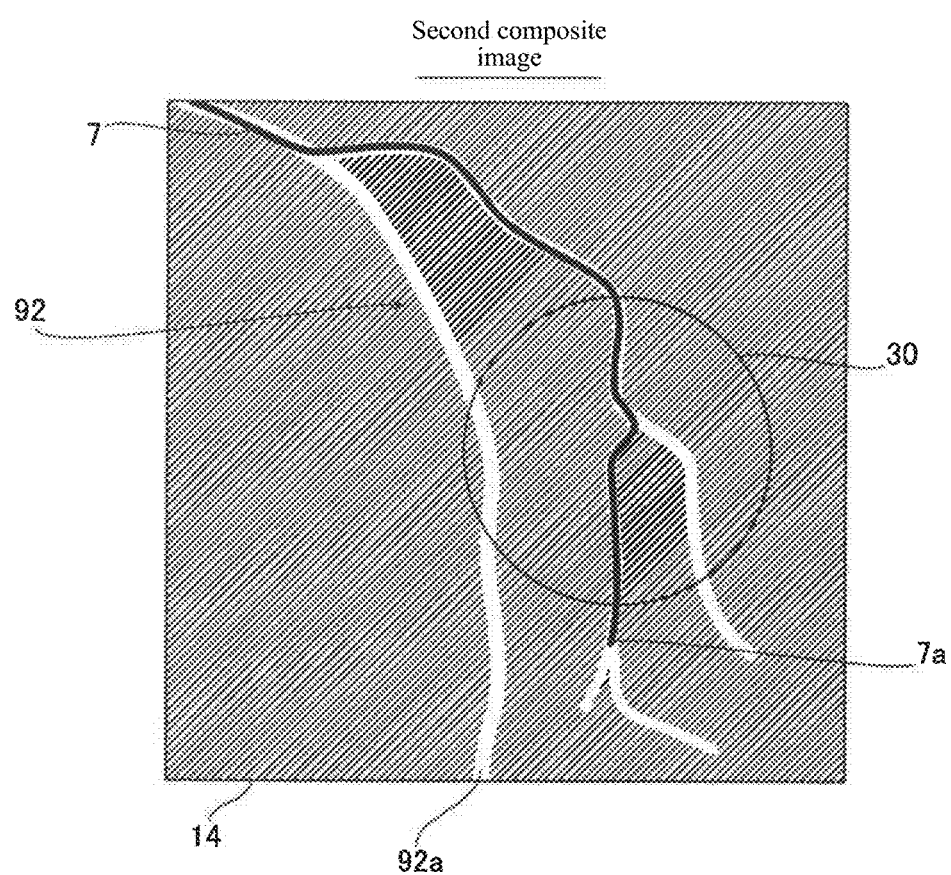
FIG. 10 is a schematic diagram for explaining a configuration in which a region of interest setting unit accepts resetting of a region of interest according to one embodiment.

When performing an operation using the device 7 such as a catheter, the blood vessel 92*a* may not have only one branch portion 92*b*, but the subsequent branch portion 92*b* may be positioned at the outside of the region of interest 30. Therefore, when the operation is proceeded, the device 7 may move from the inside of the region of interest 30 to the outside of the region of interest 30. In this embodiment, as shown in FIG. 10, the region of interest setting unit 20*d* is configured to accept the resetting of the region of interest 30 when the tip end 7*a* of the device 7 that has been reflected in the region of interest 30 is moved to the outside of the region of interest 30. In this embodiment, when the operator visually confirms that the tip end 7*a* of the device 7 has moved to the outside of the region of interest 30, an operation input for resetting the region of interest 30 is performed. It may be configured such that the control unit 20 tracks the tip end 7*a* of the device 7 by image processing and detects that the tip end 7*a* has moved to the outside of the region of interest 30. The control unit 20 may be configured to notify the operator that the region of interest 30 is to be reset when it is detected that the tip end 7*a* of the device 7 has moved to the outside of the region of interest 30.

(Generation Processing of Composite Image)

Figure 11:
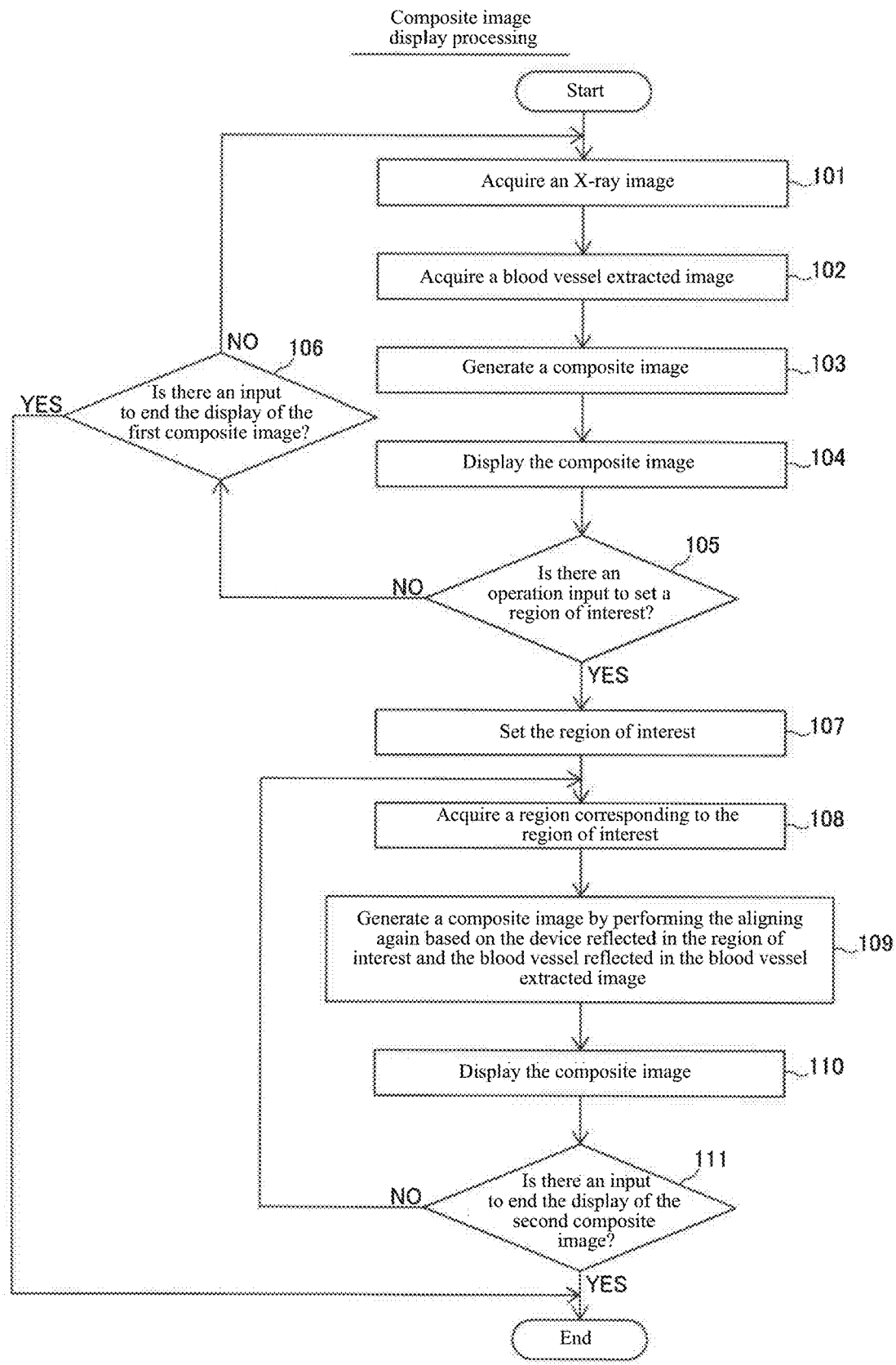
FIG. 11 is a flowchart for explaining the processing of generating a composite image.

Referring now to FIG. 11, the processing will be described in which the composite image generation unit 20*c* produces the first composite image 13 and the second composite image 14.

In Step 101, the X-ray image acquisition unit 20*a* acquires an X-ray image 10. In the processing in Step 101, the X-ray image acquisition unit 20*a* sequentially acquires the X-ray image 10 as a live image from the imaging unit 1.

In Step 102, the blood vessel extracted image acquisition unit 20*b* acquires a blood vessel extracted image 12 that has been generated in advance based on the contrast image 11 that is an X-ray image 10 captured with a contrast agent administered to the object. In the processing in Step 102, the blood vessel extracted image acquisition unit 20*b* acquires a plurality of blood vessel extracted images 12 from the storage unit 5.

In Step 103, the composite image generation unit 20*c* generates a first composite image 13 in which the X-ray image 10 captured with no contrast agent administered and the blood vessel extracted image 12 are composed with the X-ray image 10 and the blood vessel extracted image 12 aligned in the positions. Note that the first composite image 13 generated in Step 103 is generated by aligning the positions of the entire X-ray image 10 and the entire blood vessel extracted image 12. That is, the first composite image 13 generated in Step 103 is an image in which a positional deviation can occur between the device 7 and the blood vessel image 92.

In Step 104, the control unit 20 displays the first composite image 13 on the display unit 4.

In Step 105, the region of interest setting unit 20*d* determines whether or not there is an operation input to set the region of interest 30. When there is no operation input to set the region of interest 30, the processing proceeds to Step 106. When there is an operation input to set the region of interest 30, the processing proceeds to Step 107.

In Step 106, the control unit 20 determines whether or not there is an input to end the displaying of the first composite image 13. When there is no input to finish the displaying of the first composite image 13, the processing proceeds to Step 101. When there is an input to finish the displaying of the first composite image 13, the processing ends.

When the processing proceeds from Step 105 to Step 107, in Step 107, the region of interest setting unit 20*d* set a region of interest 30 which is a part of the X-ray image 10 and reflects the device 7 introduced into the blood vessel 92*a* of the object. In the processing in Step 107, the region of interest setting unit 20*d* sets a region of interest 30, based on an operation input for setting the region of interest 30.

In Step 108, the composite image generation unit 20*c* acquires a region 31 corresponding to the region of interest 30. Note that the processing in Step 108 includes the processing of selecting a blood vessel extracted image 12 caused to be aligned in the position with the X-ray image 10 by the composite image generation unit 20*c*.

In Step 109, the composite image generation unit 20*c* generates a second composite image 14 by aligning the positions of the X-ray image 10 and the blood vessel extracted image 12 again, based on the device 7 reflected in the region of interest 30 and the blood vessel image 92 reflected in the blood vessel extracted image 12.

In Step 110, the control unit 20 causes the second composite image 14 to be displayed on the display unit 4.

In Step 111, the control unit 20 determines whether or not there is an input to terminate the displaying of the second composite image 14. When there is no input to terminate the displaying of the second composite image 14, the processing proceeds to Step 108. When there is an input to finish the displaying of the second composite image 14, the processing ends.

In this embodiment, when there is no operation input to set the region of interest 30, the control unit 20 performs processing of Step 101 to Step 106 on the X-ray image 10 which is a live image, displays the first composite image 13, and displays it on the display unit 4. That is, the control unit 20 generates the first composite image 13 on a frame-by-frame basis and displays it on the display unit 4. When there is an operation input to set the region of interest 30, the control unit 20 performs the processing of Step 107 to Step 111 on the X-ray image 10 which is a live image, generates a second composite image 14, and displays it on the display unit 4. In other words, the control unit 20 generates the second composite image 14 on a frame-by-frame basis and displays it on the display unit 4.

Figure 12:
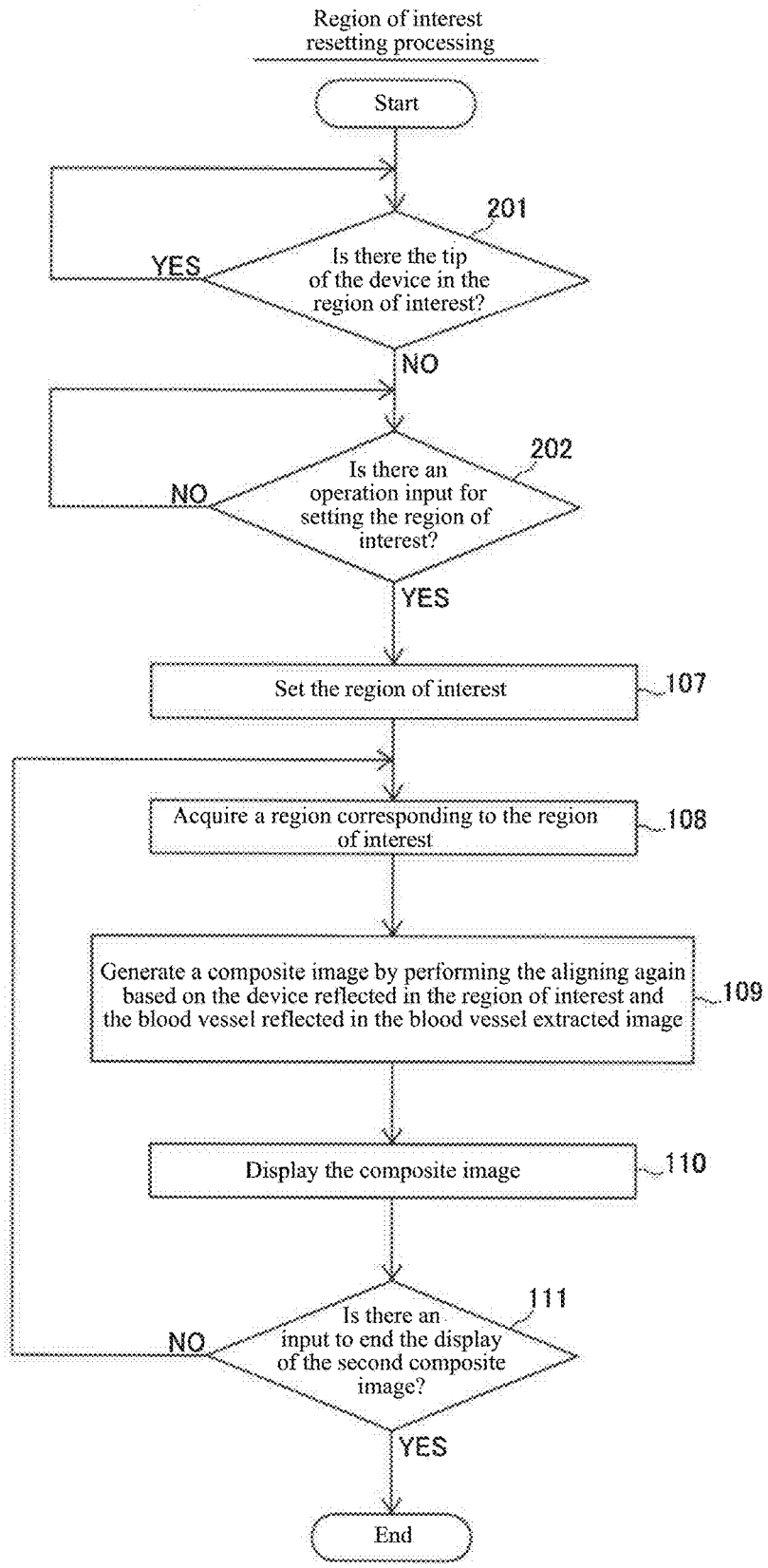
FIG. 12 is a flowchart for explaining the processing of resetting a region of interest and generating a composite image.

Next, referring to FIG. 12, the processing in which the region of interest setting unit 20*d* resets the region of interest 30 will be described. Note that the same step as that of the processing when the second composite image 14 is generated is denoted by the same reference symbol, and the detailed descriptions thereof will be omitted.

In Step 201, the region of interest setting unit 20*d* determines whether or not the tip end 7*a* of the device 7 is within the region of interest 30. When the tip end 7a of the device 7 is within the region of interest 30, the processing of Step 201 is repeated. When the tip end 7a of the device 7 is not within the region of interest 30, the processing proceeds to Step 202.

In Step 202, the region of interest setting unit 20d determines whether or not there is an operation input for setting the region of interest 30. When there is no operation input for setting the region of interest 30, the processing in Step 202 is repeated. When there is an operation input for setting the region of interest 30, the processing proceeds from Step 107 to Step 111 to generate a second composite image 14, and causes the generated second composite image 14 to be displayed on the display unit 4. Thereafter, the processing ends.

Effects of this Embodiment

In this embodiment, the following effects can be obtained.

In this embodiment, as described above, the X-ray fluoroscopic imaging apparatus 100 is provided with: an imaging unit 1 including an X-ray source 1a for irradiating an object with X-rays and an X-ray detector 1b for detecting X-rays emitted from the X-ray source 1a; an X-ray image acquisition unit 20a configured to acquire an X-ray image 10 captured by the imaging unit 1; a blood vessel extracted image acquisition unit 20b configured to acquire a blood vessel extracted image 12 in which a blood vessel image 92 of the object is extracted, the blood vessel image having been generated in advance based on a contrast image 11 that is the X-ray image 10 captured with a contrast agent administered to the object; a composite image generation unit 20c configured to generate a second composite image in which the X-ray image 10 captured with no contrast agent administered and the blood vessel extracted image are composed with the X-ray image and the blood extraction image aligned in positions; and a region of interest setting unit 20d configured to set a region of interest 30, the region of interest 30 being a part of the X-ray image 10 and reflecting a device 7 introduced into a blood vessel 92a of the object. The composite image generation unit 20c is configured to generate the second composite image 14 by composing the X-ray image 10 and the blood vessel extracted image 12 with the positions of the X-ray image 10 and the blood vessel extracted image 12 aligned, based on the device 7 reflected in the region of interest 30 set by the region of interest setting unit 20d and the blood vessel image 92 reflected in the blood vessel extracted image 12.

With this, since the aligning of the positions of the X-ray image 10 and the blood vessel extracted image 12 is performed based on the device 7 reflected in the region of interest 30 and the blood vessel image 92 reflected in the blood vessel extracted image 12, the aligning of the positions of the X-ray image 10 and the blood vessel extracted image 12 to each other can be performed with high accuracy in the vicinity of the device 7. As a result, it is possible to generate a second composite image 14 in which a positional deviation between the X-ray image 10 and the blood vessel extracted image 12 is suppressed in the vicinity of device 7.

Also, in this embodiment, as described above, the X-ray image processing method includes the steps of:
acquiring an X-ray image 10;
acquiring a blood vessel extracted image 12 generated in advance based on a contrast image 11 that is the X-ray image 10 captured with a contrast agent administered to an object by a blood vessel extracted image acquisition unit 20b;
generating a second composite image 14 in which the X-ray image 10 captured by a composite image generation unit 20c with no contrast agent administered and the blood vessel extracted image 12 with the X-ray image 10 and the blood vessel extracted image 12 aligned in positions;
setting a region of interest 30 by a region of interest setting unit 20d, the region of interest 30 being a part of the X-ray image 10 and reflecting a device 7 introduced into a blood vessel 92 of the object; and
generating the second composite image 14 by aligning the positions of the X-ray image 10 and the blood vessel extracted image 12 again, based on the device 7 reflected in the region of interest 30 and a blood vessel image 92 reflected in the blood vessel extracted image 12.

With this, similarly to the X-ray fluoroscopic imaging apparatus 100, it is possible to provide an X-ray image processing method capable of generating a second composite image 14 in which a positional deviation between the X-ray image 10 and the blood vessel extracted image 12 is suppressed in the vicinity of the device 7.

Further, in the above-described embodiment, the following further effects can be further acquired by the following configuration.

Further, in this embodiment, as described above, the composite image generation unit 20c is configured to acquire the region 31 corresponding to the region of interest 30 in the blood vessel extracted image 12, based on the shape of the device 7 reflected in the region of interest 30 and the shape of the blood vessel image 92 reflected in the blood vessel extracted image 12. Here, since the device 7 advances through the blood vessel 92a, the device 7 is reflected in a shape along the blood vessel 92a in the X-ray image 10. Therefore, the shape of the device 7 in the X-ray image 10 and the contour of the blood vessel image 92 in the blood vessel extracted image 12 or the curve passing through the center of the blood vessel image 92 coincide with each other with high accuracy. Therefore, by configuring such that the region 31 corresponding to the region of interest 30 in the blood vessel extracted image 12 is acquired based on the shape of the device 7 and the shape of the blood vessel image 92, even in a case where there is no feature point, such as, e.g., a marker, commonly reflected in the X-ray image 10 and the blood vessel extracted image 12, it is possible to acquire the region 31 corresponding to the region of interest 30. As a result, even in a case where a region of interest 30 is set to a position desired by an operator, the aligning of the positions of the X-ray image 10 and the blood vessel extracted image 12 to each other can be performed based on the shape of the device 7 and the shape of the blood vessel image 92.

Further, in this embodiment, as described above, the X-ray image acquisition unit 20a is configured to acquire, as a live image, the X-ray image 10 to be generated sequentially. The composite image generation unit 20c is configured to generate the second composite image 14 by acquiring the region 31 corresponding to the region of interest 30 in the blood vessel extracted image 12 based on the device 7 reflected in the region of interest 30 of each frame of the live image and aligning the positions of the region 31 corresponding to the region of interest 30 in the acquired blood vessel extracted image 12 and the region of interest 30 of each frame of the live image. With this, it becomes possible to generate the second composite image 14 as a moving image, and the operator can confirm the second composite image 14 as a moving image. Therefore, the operational workload of the operator can be reduced.

Further, in this embodiment, as described above, the object includes the heart 91 of the subject 90. The X-ray image acquisition unit 20a is configured to acquire a plurality of X-ray images 10 of at least one period of the heartbeat of the heart 91 as live images. The blood vessel extracted image acquisition unit 20b is configured to acquire a plurality of blood vessel extracted images 12 of at least one period of the heartbeat of the heart 91 as the blood vessel extracted image 12. The composite image generation unit 20c is configured to acquire the region 31 corresponding to the region of interest 30 from the blood vessel extracted image 12 having a phase closest to a phase of each frame of the live image in the region of interest 30 among a plurality of blood vessel extracted images 12, based on the shape of the device 7 reflected in the region of interest 30 in each frame of the live image and the shape of the blood vessel image 92 reflected in the blood vessel extracted image 12. With this, based on the phase of the heartbeat of the heart 91 in addition of the shape of the device 7 and the shape of the blood vessel 92a, it is possible to acquire the region 31 corresponding to the region of interest 30. As a result, it is possible to acquire the region 31 corresponding to the region of interest 30 highly correlated with the region of interest 30.

Further, in this embodiment, as described above, the input receiving unit 3 for receiving the operation input for setting the region of interest 30 in the X-ray image 10 is provided, and the region of interest setting unit 20d is configured to set the region of interest 30 in the X-ray image 10 based on the operation input received by the input receiving unit 3. With this, it is possible to set the region of interest 30 to a position desired by the operator, such as, e.g., the branch portion 92b of the blood vessel 92a. As a result, at the position desired by the operator, it is possible to generate the second composite image 14 high in position alignment accuracy of the X-ray image 10 and the blood vessel extracted image 12.

Further, in this embodiment, as described above, the display unit 4 for displaying the X-ray image 10 or the composite image (either the first composite image 13 or the second composite image 14) is further provided. The composite image generation unit 20c is configured to generate the second composite image by aligning the positions of the X-ray image 10 and the blood vessel extracted image 12 based on the device 7 reflected in the region of interest 30, when the region of interest 30 is set by the region of interest setting unit 20d that has received an operation input when the X-ray image 10 or the first composite image 13 is being displayed on the display unit 4. With this, in a case of selecting the blood vessel 92a into which the device 7 is introduced at the branch portion 92b of the blood vessel 92a or the like, it is possible to generate the second composite image 14 in which the X-ray image 10 and the blood vessel extracted image 12 are aligned in the positions in the region of interest 30 at a timing desired by an operator.

Further, in this embodiment, as described above, the region of interest setting unit 20d is configured to set the region of interest 30 having a size corresponding to the moving range of the device 7 when the device 7 moves in accordance with the heartbeat of the heart 91 to the live image. As a result, even in a case where the device 7 has been moved in accordance with the heartbeat of the heart 91, it is possible to assuredly suppress the device 7 from moving to the outside of the region of interest 30. As a result, even in a case where the device 7 has been moved, the second composite image 14 in which the X-ray image 10 and the blood vessel extracted image 12 are aligned in the positions can be generated at the position of the device 7.

Further, in this embodiment, as described above, the region of interest setting unit 20d is configured to receive the resetting of the region of interest 30 when the tip end 7a of the device 7, which is reflected in the region of interest 30, has been moved to the outside of the region of interest 30. As a result, even in a case where the tip end 7a of the device 7 has been moved by the operation, by resetting the region of interest 30 so as to include the tip end 7a of the device 7, it is possible to align the positions of the X-ray image 10 and the blood vessel extracted image 12 at the tip end 7a of the device 7 with high accuracy and compose the X-ray image 10 and the blood vessel extracted image 12 to generate the second composite image 14. As a result, by resetting the region of interest 30 in accordance with the movement of the device 7, the operator can generate the second composite image 14 with high accuracy at the desired position, thereby improving the usability of the operator.

In addition, in this embodiment, as described above, the device 7 includes at least one of a catheter, a stent, and a guidewire introduced into the blood vessel 92a. With this, in the second composite image 14, the operator can easily visually recognize at least one of a catheter, a stent, and a guidewire introduced into the blood vessel 92a. Consequently, in the operation performed by introducing at least one of the catheter, the stent, and the guidewire into the blood vessel 92a, the workload of the operator can be reduced.

Modifications

It should be understood that the embodiments disclosed here are examples in all respects and are not restrictive. The scope of the present invention is shown by the claims rather than the descriptions of the embodiments described above, and includes all changes (modifications) within the meaning of equivalent to claims.

For example, in the above embodiment, an example is shown in which it is configured such that the X-ray fluoroscopic imaging apparatus 100 is provided with the input receiving unit 3, but the present invention is not limited thereto. In the present invention, for example, the X-ray fluoroscopic imaging apparatus 100 may not be provided with an input receiving unit 3. In a case where the X-ray fluoroscopic imaging apparatus 100 is not provided with the input receiving unit 3, for example, the control unit 20 may be provided with a device detection unit for detecting the tip end 7a of the device 7 by the image processing or the like. The region of interest setting unit 20d may be configured to set the region of interest 30 in the vicinity of the tip end 7a of the device 7 detected by the device detection unit.

In the above-described embodiment, an example is shown in which it is configured such that the X-ray fluoroscopic imaging apparatus 100 is provided with the display unit 4, but the present invention is not limited thereto. In the present invention, the X-ray fluoroscopic imaging apparatus 100 may not be provided with the display unit 4. In a case where the X-ray fluoroscopic imaging apparatus 100 is not provided with the display unit 4, the control unit 20 may be configured to display the second composite image 14 on an external display device or the like.

In the above embodiment, an example is shown in which it is configured such that the composite image generation unit 20c generates, as the second composite image 14, a moving image in which the device 7 moves within the region of interest 30, but the present invention is not limited thereto.

For example, the composite image generation unit 20c may be configured to generate, as the second composite image 14, a moving image in which the device 7 is reflected in the region of interest 30 in a stationary state.

Further, in the above-described embodiment, an example is shown in which it is configured such that the composite image generation unit 20c generates the second composite image 14 as a moving image, but the present invention is not limited thereto. In the present invention, the composite image generation unit 20c may be configured to generate the second composite image 14 as a still image.

Further, in the above-described embodiment, an example is shown in which it is configured such that the composite image generation unit 20c generates the first composite image 13, but the present invention is not limited thereto. In the present invention, it may be configured such that the composite image generation unit 20c does not generate the first composite image 13.

Further, in the above-described embodiment, an example is shown in which the blood vessel 92a of the heart 91 of the subject 90 is imaged as an object, but the present invention is not limited thereto. In the present invention, a pulmonary blood vessel, etc., may be imaged. At the time of the imaging, in the case of imaging an object that moves by a heartbeat, a respiration, or the like, it is preferable to use the X-ray fluoroscopic imaging apparatus 100.

In the above-described embodiment, an example is shown in which the region of interest setting unit 20d sets a circular region as the region of interest 30, but the present invention is not limited thereto. The shape of the region of interest 30 set by the region of interest setting unit 20d may be a rectangular shape or a star shape. The shape of the region of interest 30 set by the region of interest setting unit 20d may be any shape. The region of interest 30 may be set a shape following a freehand trajectory entered by an operator.

Further, in the above-described embodiment, an example is shown in which it is configured such that the region of interest setting unit 20d sets the region of interest 30 having a predetermined size, but the present invention is not limited thereto. For example, in the present invention, the region of interest setting unit 20d may be configured to set any size of the region of interest 30 based on an operation input of an operator.

[Aspects]

It will be understood by those skilled in the art that the above-described exemplary embodiments are concrete examples of the following aspects.

(Item 1)

An X-ray fluoroscopic imaging apparatus comprising:
an imaging unit including an X-ray source for irradiating an object with X-rays and an X-ray detector for detecting X-rays emitted from the X-ray source;
an X-ray image acquisition unit configured to acquire an X-ray image captured by the imaging unit;
a blood vessel extracted image acquisition unit configured to acquire a blood vessel extracted image in which a blood vessel image of the object is extracted, the blood vessel image having been generated in advance based on a contrast image that is the X-ray image captured with a contrast agent administered to the object;
a composite image generation unit configured to generate a composite image in which the X-ray image captured with no contrast agent administered and the blood vessel extracted image are composed with the X-ray image and the blood vessel extracted image aligned in positions; and
a region of interest setting unit configured to set a region of interest, the region of interest being a part of the X-ray image and reflecting a device introduced into a blood vessel of the object,
wherein the composite image generation unit is configured to generate the composite image by aligning positions of the X-ray image and the blood vessel extracted image, based on the device reflected in the region of interest set by the region of interest setting unit and the blood vessel image reflected in the blood vessel extracted image.

(Item 2)

The X-ray fluoroscopic imaging apparatus as recited in the above-described Item 1,
wherein the composite image generation unit is configured to acquire a region corresponding to the region of interest in the blood vessel extracted image, based on a shape of the device reflected in the region of interest and a shape of the blood vessel image reflected in the blood vessel extracted image.

(Item 3)

The X-ray fluoroscopic imaging apparatus as recited in the above-described Item 2,
wherein the X-ray image acquisition unit is configured to acquire the X-ray image to be sequentially generated as a live image, and wherein the composite image generation unit is configured to generate the composite image by acquiring a region corresponding to the region of interest in the blood vessel extracted image based on the device reflected in the region of interest of each frame of the live image and aligning positions of the region corresponding to the region of interest in the acquired blood vessel extracted image and the region of interest of each frame of the live image.

(Item 4)

The X-ray fluoroscopic imaging apparatus as recited in the above-described Item 3,
wherein the object includes a heart of a subject,
wherein the X-ray image acquisition unit is configured to acquire, as the live image, at least a plurality of X-ray images for one period of a heartbeat of the heart,
wherein the blood vessel extracted image acquisition unit is configured to acquire, as the blood vessel extracted image, at least a plurality of blood vessel extracted images for one period of the heartbeat of the heart, and
wherein the composite image generation unit is configured to acquire the region corresponding to the region of interest from the blood vessel extracted image having a phase closest to a phase of each frame of the live image in the region of interest among a plurality of blood vessel extracted images, based on the shape of the device reflected in the region of interest in each frame of the live image and the shape of the blood vessel image reflected in the blood vessel extracted image.

(Item 5)

The X-ray fluoroscopic imaging apparatus as recited in the above-described Item 2, further comprising:
an input receiving unit configured to receive an operation input for setting the region of interest in the X-ray image,
wherein the region of interest setting unit is configured to set the region of interest in the X-ray image, based on the operation input received by the input receiving unit.

(Item 6)

The X-ray fluoroscopic imaging apparatus as recited in the above-described Item 5, further comprising:

a display unit configured to display the X-ray image or the composite image, wherein the composite image generation unit is configured to generate the composite image by aligning positions of the X-ray image and the blood vessel extracted image based on the device reflected in the region of interest, when the region of interest is set by the region of interest setting unit that has received the operation input when the X-ray image or the composite image is being displayed on the display unit.

(Item 7)

The X-ray fluoroscopic imaging apparatus as recited in the above-described Item 4, wherein the region of interest setting unit is configured to set the region of interest of a size corresponding to a moving range of the device when the device moves in accordance with the heartbeat of the heart to the live image.

(Item 8)

The X-ray fluoroscopic imaging apparatus as recited in the above-described Item 1, wherein the region of interest setting unit is configured to accept resetting of the region of interest when a tip end of the device reflected in the region of interest has moved to an outside of the region of interest.

(Item 9)

The X-ray fluoroscopic imaging apparatus as recited in the above-described Item 1, wherein the device includes at least one of a catheter, a stent, and a guidewire introduced into the blood vessel.

(Item 10)

An X-ray image processing method comprising the steps of:

acquiring an X-ray image;

acquiring a blood vessel extracted image generated in advance based on a contrast image that is the X-ray image captured with a contrast agent administered to an object by a blood vessel extracted image acquisition unit;

generating a composite image in which the X-ray image captured with no contrast agent administered and the blood vessel extracted image are composed with the X-ray image and the blood vessel extracted image aligned in positions by a composite image generation unit;

setting a region of interest by a region of interest setting unit, the region of interest being a part of the X-ray image and reflecting a device introduced into a blood vessel of the subject; and generating the composite image by aligning positions of the X-ray image and the blood vessel extracted image again, based on the device reflected in the region of interest and a blood vessel image reflected in the blood vessel extracted image.

The invention claimed is:

1. An X-ray fluoroscopic imaging apparatus comprising:

an imaging unit including an X-ray source for irradiating an object with X-rays and an X-ray detector for detecting X-rays emitted from the X-ray source;

an X-ray image acquisition unit configured to acquire an X-ray image captured by the imaging unit;

a blood vessel extracted image acquisition unit configured to acquire a blood vessel extracted image in which a blood vessel image of the object is extracted, the blood vessel image having been generated in advance based on a contrast image that is the X-ray image captured with a contrast agent administered to the object;

a composite image generation unit configured to generate a first composite image in which the X-ray image captured with no contrast agent administered and the blood vessel extracted image are composed with the X-ray image and the blood vessel extracted image aligned in positions; and a region of interest setting unit configured to set a region of interest, the region of interest being a part of the X-ray image and reflecting a device introduced into a blood vessel of the object, wherein the composite image generation unit is configured to generate a second composite image by aligning positions of the X-ray image and the blood vessel extracted image, based on the device reflected in the region of interest set by the region of interest setting unit and the blood vessel image reflected in the blood vessel extracted image.

2. The X-ray fluoroscopic imaging apparatus as recited in claim 1, wherein the composite image generation unit is configured to acquire a region corresponding to the region of interest in the blood vessel extracted image, based on a shape of the device reflected in the region of interest and a shape of the blood vessel image reflected in the blood vessel extracted image.

3. The X-ray fluoroscopic imaging apparatus as recited in claim 2, wherein the X-ray image acquisition unit is configured to acquire the X-ray image to be sequentially generated as a live image, and wherein the composite image generation unit is configured to generate the second composite image by acquiring a region corresponding to the region of interest in the blood vessel extracted image based on the device reflected in the region of interest of each frame of the live image and aligning positions of the region corresponding to the region of interest in the acquired blood vessel extracted image and the region of interest of each frame of the live image.

4. The X-ray fluoroscopic imaging apparatus as recited in claim 3, wherein the object includes a heart of a subject, wherein the X-ray image acquisition unit is configured to acquire, as the live image, at least a plurality of X-ray images for one period of a heartbeat of the heart, wherein the blood vessel extracted image acquisition unit is configured to acquire, as the blood vessel extracted image, at least a plurality of blood vessel extracted images for one period of the heartbeat of the heart, and wherein the composite image generation unit is configured to acquire the region corresponding to the region of interest from the blood vessel extracted image having a phase closest to a phase of each frame of the live image in the region of interest among a plurality of blood vessel extracted images, based on the shape of the device reflected in the region of interest in each frame of the live image and the shape of the blood vessel image reflected in the blood vessel extracted image.

5. The X-ray fluoroscopic imaging apparatus as recited in claim 2, further comprising:

an input receiving unit configured to receive an operation input for setting the region of interest in the X-ray image, wherein the region of interest setting unit is configured to set the region of interest in the X-ray image, based on the operation input received by the input receiving unit.

6. The X-ray fluoroscopic imaging apparatus as recited in claim 5, further comprising:
a display unit configured to display the X-ray image, the first composite image, or the second composite image,
wherein the composite image generation unit is configured to generate the second composite image by aligning positions of the X-ray image and the blood vessel extracted image based on the device reflected in the region of interest, when the region of interest is set by the region of interest setting unit that has received the operation input when the X-ray image or the first composite image is being displayed on the display unit.

7. The X-ray fluoroscopic imaging apparatus as recited in claim 4,
wherein the region of interest setting unit is configured to set the region of interest of a size corresponding to a moving range of the device when the device moves in accordance with the heartbeat of the heart to the live image.

8. The X-ray fluoroscopic imaging apparatus as recited in claim 1,
wherein the region of interest setting unit is configured to accept resetting of the region of interest when a tip end of the device reflected in the region of interest has moved to an outside of the region of interest.

9. The X-ray fluoroscopic imaging apparatus as recited in claim 1,
wherein the device includes at least one of a catheter, a stent, and a guidewire introduced into the blood vessel.

10. An X-ray image processing method comprising the steps of:
acquiring an X-ray image;
acquiring a blood vessel extracted image generated in advance based on a contrast image that is the X-ray image captured with a contrast agent administered to an object by a blood vessel extracted image acquisition unit;
generating a first composite image in which the X-ray image captured with no contrast agent administered and the blood vessel extracted image are composed with the X-ray image and the blood vessel extracted image aligned in positions by a composite image generation unit;
setting a region of interest by a region of interest setting unit, the region of interest being a part of the X-ray image and reflecting a device introduced into a blood vessel of the object; and
generating a second composite image by aligning positions of the X-ray image and the blood vessel extracted image again, based on the device reflected in the region of interest and a blood vessel image reflected in the blood vessel extracted image.

11. An X-ray fluoroscopic imaging apparatus comprising:
an imaging unit including an X-ray source for irradiating an object with X-rays and an X-ray detector for detecting X-rays emitted from the X-ray source; and
a processor,
wherein the processor includes:
an X-ray image acquisition unit configured to acquire an X-ray image captured by the imaging unit,
a blood vessel extracted image acquisition unit configured to acquire a blood vessel extracted image in which a blood vessel image of the object is extracted, the blood vessel image having been generated based on a contrast image that is captured with a contrast agent administered to the object among the X-ray image acquired by the X-ray image acquisition unit,
a region of interest setting unit configured to set a region of interest for a non-contrast image that is captured without the contrast agent administered to the object among the X-ray image acquired by the X-ray image acquisition unit, the region of interest reflecting a device introduced into a blood vessel of the object, and
a composite image generation unit configured to generate the composite image by aligning positions of the non-contrast image and the blood vessel extracted image, based on the device reflected in the region of interest set by the region of interest setting unit and the blood vessel image reflected in the blood vessel extracted image.

* * * * *